United States Patent
Lyles

(10) Patent No.: US 7,247,721 B2
(45) Date of Patent: *Jul. 24, 2007

(54) MATERIALS AND METHODS FOR BINDING NUCLEIC ACIDS TO SURFACES

(76) Inventor: Mark B. Lyles, 9127 Cap Mountain Dr., San Antonio, TX (US) 78255

(*) Notice: Subject to any disclaimer, the term of this patent is extended or adjusted under 35 U.S.C. 154(b) by 0 days.

This patent is subject to a terminal disclaimer.

(21) Appl. No.: 11/057,440

(22) Filed: Feb. 14, 2005

(65) Prior Publication Data

US 2005/0148067 A1 Jul. 7, 2005

Related U.S. Application Data

(63) Continuation of application No. 09/910,697, filed on Jul. 20, 2001, now Pat. No. 6,855,817.

(60) Provisional application No. 60/220,096, filed on Jul. 21, 2000.

(51) Int. Cl.
- C07H 19/00 (2006.01)
- C07H 19/16 (2006.01)
- C07H 19/173 (2006.01)
- C07H 21/00 (2006.01)
- C07D 473/00 (2006.01)

(52) U.S. Cl. ............ 536/25.4; 536/27.12; 536/27.21; 536/27.8; 536/26.23; 544/267

(58) Field of Classification Search ............ 536/25.4, 536/27.12, 27.21, 27.8, 26.23; 544/267
See application file for complete search history.

(56) References Cited

U.S. PATENT DOCUMENTS

| | | | | |
|---|---|---|---|---|
| 2,996,435 A | * | 8/1961 | Ehrlich et al. | 435/116 |
| 3,030,388 A | * | 4/1962 | Moore et al. | 552/12 |
| 3,433,782 A | * | 3/1969 | Kreiser | 536/25.4 |
| 3,821,193 A | * | 6/1974 | Fare et al. | 536/23.1 |
| 4,623,723 A | * | 11/1986 | Keller et al. | 536/25.4 |
| 4,699,717 A | * | 10/1987 | Riesner et al. | 536/25.4 |
| 4,921,952 A | * | 5/1990 | Longmire et al. | 536/25.41 |
| 4,923,978 A | * | 5/1990 | McCormick | 536/25.4 |
| 4,925,572 A | * | 5/1990 | Pall | 210/767 |
| 4,935,342 A | * | 6/1990 | Seligson et al. | 435/6 |
| 4,952,572 A | * | 8/1990 | Ohkuma et al. | 514/279 |
| 4,997,932 A | * | 3/1991 | Reardon et al. | 536/25.4 |
| 5,057,426 A | * | 10/1991 | Henco et al. | 435/270 |
| 5,075,430 A | * | 12/1991 | Little | 536/25.41 |
| 5,342,931 A | * | 8/1994 | Woodard et al. | 536/25.4 |
| 5,658,548 A | * | 8/1997 | Padhye et al. | 423/335 |
| 5,808,041 A | * | 9/1998 | Padhye et al. | 536/25.4 |
| 6,020,186 A | * | 2/2000 | Henco et al. | 435/287.2 |
| 6,037,465 A | * | 3/2000 | Hillebrand et al. | 536/25.42 |
| 6,855,817 B2 | * | 2/2005 | Lyles | 536/25.4 |

FOREIGN PATENT DOCUMENTS

| | | |
|---|---|---|
| JP | 5/333015 A | * 12/1993 |
| WO | WO95/06056 A1 | * 3/1995 |
| WO | WO95/34569 A1 | * 12/1995 |

OTHER PUBLICATIONS

[R] Maskos et al., "Oligonucleotide Hybridisations on Glass Supports: A Novel Linker for Oligonucleotide Synthesis and Hybridisation Properties of Oligonucleotides Synthesized in situ," Nucleic Acids Research, 20(7), 1679-1684 (1992).*
(S) M. Leonard, "New Packing Materials for Protein Chromatography," Journal of Chromatography B, 699, 3-27 (Oct. 1997).*
(T) Cloarec et al., "Functionalization of Si/SiO2 Substrates with Homooligonucleotides for a DNA Biosensor," Sensors and Actuators B, 58(1-3), 394-398 (Sep. 1998).*
(U) O'Donnell-Maloney et al., "Microfabrication and Array Technologies for DNA Sequencing and Diagnostics," Genetic Analysis: Biomolecular Engineering, 13(6), 1541-157 (Dec. 1996).*
PCT International Search Report on Patentability for PCT/US01/23079;79 pgs, Jul. 20, 2001.

* cited by examiner

*Primary Examiner*—S. Anna Jiang
*Assistant Examiner*—L. E. Crane
(74) *Attorney, Agent, or Firm*—Baker Botts, L.L.P.

(57) ABSTRACT

Surfaces containing high purity silica (silicon dioxide) exhibit high loading potential for nucleic acids.

Formulations containing nucleic acids and materials which mask the electrostatic interactions between the nucleic acids and surfaces are disclosed. By masking the phosphate charges of the nucleic acids, undesired interactions may be minimized or eliminated, thereby allowing the covalent bonding of the nucleic acids to the surface to proceed. The use of such formulations additionally minimizes nonspecific binding of the nucleic acids to the surface. Examples of materials to be included in such formulations include cations, xanthines, hexoses, purines, arginine, lysine, polyarginine, polylysine, and quaternary ammonium salts.

14 Claims, No Drawings

MATERIALS AND METHODS FOR BINDING NUCLEIC ACIDS TO SURFACES

CROSS REFERENCE TO RELATED APPLICATIONS

This application is a continuation of U.S. patent application Ser. No. 09/910,697 filed Jul. 20, 2001, and entitled "Materials and Methods for Binding Nucleic Acids to Surfaces," now U.S. Pat. No. 6,855,817, which claims priority to U.S. Provisional Patent Application Ser. No. 60/220,096 filed Jul. 21, 2000, and entitled "Materials and Methods for Binding Nucleic Acids to Surfaces."

FIELD OF THE INVENTION

The invention relates to silica surfaces useful for binding nucleic acids, and formulations to improve the binding of nucleic acids to surfaces. In particular, high purity silica (silicon dioxide) surfaces are disclosed. Additionally, nucleic acid formulations containing materials which mask the electrostatic interactions between nucleic acids and surfaces are disclosed.

BACKGROUND OF THE INVENTION

The binding of nucleic acids, especially DNA, to surfaces has been reported many times in the scientific literature. Binding may be accomplished either through non-specific electrostatic or hydrophobic means, or through formation of covalent bonds to the terminus of the nucleic acid.

Covalent bonding of nucleic acids to surfaces is generally preferred, as it specifically orients the nucleic acids in a given manner. The bonded nucleic acids may be used for hybridization experiments when contacted with other nucleic acids in solution.

Traditionally, glass has been used as the substrate for binding nucleic acids. The glass is heated in order to produce slides or beads. During heating, impurities tend to migrate towards the surface of the material, reducing the surface area available for binding nucleic acids.

Electrostatic interactions between the nucleic acids and the surface result in a fraction of the nucleic acids becoming nonspecifically bound to the surface. This may result in nucleic acids "laying down" or orienting themselves parallel to the surface, rather than being perpendicular to the surface. This orientation reduces or eliminates the ability of the bound nucleic acid to interact with other nucleic acids in solution, and additionally may result in the blockage of other covalent bonding sites on the surface.

There exists a need for improved materials for the preparation of nucleic acids bound to surfaces, and methods to improve the specific covalent bonding of nucleic acids to surfaces.

SUMMARY OF THE INVENTION

Surfaces containing high purity silica (silicon dioxide) exhibit high loading potential for nucleic acids.

Formulations containing nucleic acids and materials which mask the electrostatic interactions between the nucleic acids and surfaces are disclosed. By masking the phosphate charges of the nucleic acids, undesired interactions may be minimized or eliminated, thereby allowing the covalent bonding of the nucleic acids to the surface to proceed. The use of such formulations additionally minimizes nonspecific binding of the nucleic acids to the surface. Examples of materials to be included in such formulations include cations, xanthines, hexoses, purines, arginine, lysine, polyarginine, polylysine, and quaternary ammonium salts. Other materials such as amines may be used if the pH of the formulation is such that the material is positively charged.

DETAILED DESCRIPTION OF THE INVENTION

The prior art materials and formulations have been plagued with two general problems; a) low loading potential of the surfaces; and b) nonspecific binding of nucleic acids to the surface.

A first embodiment of the invention relates to the use of substantially pure silica (silicon dioxide) in surfaces. As there are essentially no impurities in the material, essentially the entire surface of the material is available for binding nucleic acids. Preferably the material is at least about 70% pure, about 80% pure, about 90% pure, about 95% pure, about 96% pure, about 97% pure, about 98% pure, about 99% pure, about 99.5% pure, about 99.9% pure, and ideally about 100% pure by weight. The resulting surface will exhibit higher loading potential for nucleic acids than does conventional glass surfaces. At a microscopic level, the silica surface preferably has a three dimensional structure, and is not planar. An example of a three dimensional structure is an array of silica fibers.

The surface may be generally be any shape, and preferably is macroscopically planar (e.g. a chip or disk) or three dimensional (e.g. a sphere or bead).

The surface properties of the materials may be modified by chemical reactions. Examples include modifying the hydrophobicity or hydrophilicity of the materials.

The surface may be constructed entirely of the substantially pure silica, or may comprise a layer of substantially pure silica mounted on top of a flat surface such as glass or metal. The substantially pure silica may be adhered to the flat surface by an adhesive, applied using a solvent, or cast directly onto the flat surface.

Substantially pure silica may be purchased from a commercial supplier, may be prepared de novo, or may be prepared by purifying silica containing impurities. Methods for treating and purifying silica fibers are taught in U.S. Pat. No. 5,951,295. These methods may be used to purify commercial or prepared silica materials so as to render them substantially pure. The purified silica materials may then be used to prepare the surfaces described herein.

The surface may be used to bind generally any nucleic acids, preferably DNA or RNA, and more preferably DNA. The nucleic acids may be bound to the surface using any acceptable chemical method. Chemical reactions for the covalent bonding of nucleic acids to surfaces containing silica are known in the art.

An additional embodiment of the invention relates to formulations suitable for the binding of nucleic acids to surfaces. Formulations are prepared comprising nucleic acids and a charged material. The charged material preferably is partially or fully cationic. The charged material may generally be any partially or fully positively charged material suitable for interaction with the phosphate groups of nucleic acids. Examples of suitable charged materials include xanthines, hexoses, purines, arginine, lysine, polyarginine, polylysine, and quaternary ammonium salts. The xanthine may generally be any xanthine, and preferably is xanthine, 1,3,7-trimethylxanthine(caffeine), 1,3,9-trimethylxanthine, 1,3-diethyl-7-methylxanthine, 1,3-diethyl-8- phenylxanthine, 1,3-dimethyl-7-(2-hydroxyethyl)xanthine, 1,3-dimethylxanthine-7-acetic acid, 1,3-dipropyl-7-methylxanthine, 1,3-dipropyl-8-p-sulfophenylxanthine, 1,7-dimethylxanthine, 1,7-dimethylxanthine (paraxanthine), 1,9-dimethylxanthine, 1-allyl-3,7-dimethyl-8-phenylxanthine, 1-allyl-3,7-dimethyl-8-p-sulfophenylxanthine, 1-butyl-4,5-dihydro-3-ethyl-8-hydroxyxanthine, 1-ethyl-3-isobutylxanthine, 1-methylxanthine, 2,6-dithiopurine, 2'-deoxyinosine, 3,7-dimethyl-1-propargylxanthine, 3,7-dimethylxanthine, 3,8-dimethyl-2-thioxanthine, 3,9-dimethylxanthine, 3-allyl-1-ethyl-8-hydroxyxanthine, 3-cyclopropyl-1-ethyl-8-hydroxyxanthine, 3-ethyl-1-propylxanthine, 3-ethyl-8-hydroxy-1-methylxanthine, 3-isobutyl-1-methylxanthine, 3-isobutyl-1-methylxanthine, 3-isobutyl-1-methylxanthine, 3-isobutyl-1-methylxanthine, 3-methyl-1-(5-oxohexyl)-7-propylxanthine, 3-methyl-8-phenyl-2-thiohypoxanthine, 3-methylxanthine, 3-propylxanthine, 6-thiohypoxanthine, 6-thioxanthine, 7-methylxanthine, 8-(3-carboxypropyl)-1,3-dimethylxanthine, 8-azaxanthine monohydrate, 8-bromo-1,3-diethylxanthine, 8-cyclopentyl-1,3-dimethylxanthine, 8-cyclopentyl-1,3-dipropylxanthine, 8-methoxymethyl-3-isobutyl-1-methylxanthine, 8-methylxanthine, 9-methylxanthine, azaserine-hypoxanthine, hypoxanthine, hypoxanthine 9-beta-d-arabinofuranoside, hypoxanthine 9-d-ribofuranoside (inosine), nicotinamide hypoxanthine dinucleotide phosphate, nicotinamide hypoxanthine dinucleotide phosphate disodium salt, nicotinamide hypoxanthine dinucleotide sodium salt, selenohypoxanthine, or xanthosine. The hexose may generally be any hexose, and preferably is alose, altrose, fructose, galactose, glucose, mannose, sorbose, tagatose, or talose, and more preferably is glucose. The hexose may be the D- or L-isomer. The purine may generally be any purine, and preferably is purine, 6-purinecarbonitrile, 6-purinethiol, or 6-purinethiol riboside. The quaternary ammonium salt may generally be any quaternary ammonium salt, and preferably is benzyltriethyl ammonium chloride (BTEAC), benzyltrimethyl ammonium chloride (BTMAC), benzyltributyl ammonium chloride (BTBAC), tetrabutyl ammonium bromide (TBAB), tetramethyl ammonium chloride (TMAC), tetrabutyl ammonium hydrogensulfate (TBAHS), trioctylmethyl ammonium chloride (TOMAC), N-lauryl pyridinium chloride (PYLC), or N-alkyl-(pyridinium/picolinium) chloride.

The charged material may serve multiple roles in the formulation, e.g. a surfactant may also interact with the phosphate groups of nucleic acids. The charged material may be affected by the pH of the formulation, e.g. amines may be protonated at low pH and deprotonated at high pH. The formulation is preferably a homogeneous mixture, and more preferably is a homogeneous aqueous mixture.

The charged material "masks" the charged phosphate groups of the nucleic acids, reducing or eliminating the potential for nonspecific binding of the nucleic acids to the silica surface by electrostatic attraction. As a result, the amount of nucleic acids nonspecifically binding to the surface is reduced or eliminated.

An additional embodiment of the invention is a method for the binding of nucleic acids to a surface. The method generally involves contacting the above described formulation with a surface containing silica. A particularly preferred embodiment involves contacting the above described formulation with a surface consisting essentially of silica. Any acceptable chemical methodology may be used to covalently bond the nucleic acids to the surface in the presence of the formulation.

The charged material in the formulation reduces nonspecific binding of the nucleic acids to the surface relative to nonspecific binding of nucleic acids to the surface in the absence of the charged material. Preferably, the method substantially eliminates nonspecific binding of the nucleic acids to the surface, and more preferably eliminates nonspecific binding of the nucleic acids to the surface. After the contacting step, the charged material may be removed, e.g. by a washing step.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A method for binding nucleic acids to a surface, the method comprising:
   providing a mixture comprising nucleic acids and a charged material comprising any cationic purine; and
   contacting the mixture and a surface to produce a bound material, wherein the bound material comprises nucleic acids covalenty bounded to the surface.

2. The method of claim 1, wherein the charged material is a cationic purine or a partially cationic purine.

3. The method of claim 1, wherein said cationic purine is a cation of a compound selected from purine, 6-purinecarbonitrile, 6-purinethiol, and 6-purinethiol riboside.

4. The method of claim 1, wherein the surface consists essentially of silica.

5. The method of claim 1, wherein the surface consists of silica.

6. The method of claim 1, further comprising removing the charged material after the contacting step.

7. The method of claim 1, wherein the nucleic acids are DNA.

8. The method of claim 1, wherein the material is a flat surface.

9. The method of claim 1, wherein the material is a bead.

10. The method of claim 1, wherein the material is an array of fibers.

11. The method of claim 4, wherein the silica is at least about 80% pure silicon dioxide.

12. The method of claim 4, wherein the silica is at least about 90% pure silicon dioxide.

13. The method of claim 4, wherein the silica is at least about 95% pure silicon dioxide.

14. The method of claim 4, wherein the silica is pure silicon dioxide.

* * * * *